United States Patent [19]

Hara

[11] Patent Number: 4,613,672

[45] Date of Patent: Sep. 23, 1986

[54] PROCESS FOR THE PRODUCTION OF TEA CATECHINS

[75] Inventor: Yukihiko Hara, Shizuoka, Japan

[73] Assignee: Mitsu Norin Co., Ltd., Tokyo, Japan

[21] Appl. No.: 624,943

[22] Filed: Jun. 27, 1984

[30] Foreign Application Priority Data

Jul. 5, 1983 [JP] Japan ............................ 58-120963

[51] Int. Cl.$^4$ .......................................... C07D 311/04
[52] U.S. Cl. ........................................................ 549/399
[58] Field of Search ........................................ 549/399

[56] References Cited

U.S. PATENT DOCUMENTS 4,105,784  8/1978  Okada ................................. 549/399
4,515,804  5/1985  Marti et al. ........................ 549/399

FOREIGN PATENT DOCUMENTS 0015417  2/1978  Japan ................................... 549/399

OTHER PUBLICATIONS

Sanderson, "The Chemistry of Tea and Tea Manufacturing", Advances in Phytochemistry, No. 5 (1971) pp. 250-255, 265-266 and 271-277.
R. F. Smith, Studies on the Formation and Composition of "Cream", in Tea Infusions, J. Sci. Fd Agric. 1968, vol. 19, Sep., pp. 530-534.
Chemical Abstracts 69:77066h (1968).
Chem. Abstracts 80:119307x (1974).
Chem. Abstracts 76:70341(e) (1972).
Chem. Abstracts 96:6481m (1982).
Chem. Abstracts 77:58728z (1975).

Primary Examiner—Ethel G. Love
Attorney, Agent, or Firm—Frishauf, Holtz, Goodman & Woodward

[57] ABSTRACT

Process for production of tea catechins selected from (−) epicatechin, (−) epigallocatechin, (−) epicatechin gallate and (−) epigallocatechin gallate comprising extracting tea leaves with hot water or an aqueous solution of methanol, ethanol or acetone, washing the extract containing solution with chloroform, transferring the washed solution into an organic solvent, removing the solution and passing the resulting solution through a reversed phase column in the presence of an eluting solution. Tea catechins and methods of using the same are also disclosed.

18 Claims, 17 Drawing Figures

PROCESS FOR THE PRODUCTION OF TEA CATECHINS

BACKGROUND OF THE INVENTION

In the course of extensive studies on the pharmaceutical effects of tea components, it has been found that tea catechins, which are major components of so-called tea tannin, possess strong physiological activity. As a result of further investigations, a novel method has been discovered which enables the production of tea catechins with high efficiency and methods of using the tea catechins are also disclosed.

SUMMARY OF THE INVENTION

The present invention relates to a process for producing tea catechins represented by the structural formula:

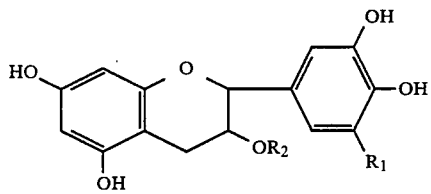

(wherein $R_1$ is a hydrogen atom or a hydroxyl group, and $R_2$ is a hydrogen atom or a group:

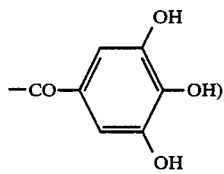

which comprises the steps of:
extracting tea leaves with hot water or a solvent selected from a group consisting of a 40–75% aqueous solution of methanol, a 40–75% aqueous solution of ethanol and a 30–80% aqueous solution of acetone to obtain an extract-containing solution;
washing the extract-containing solution with chloroform to make the solution free of impurities such as caffeine and chlorophyll;
contacting the washed solution with an organic solvent to transfer the extract into said organic solvent;
distilling away the organic solvent to yield a concentrated solution containing the extract; and
passing the concentrated solution through a reversed phase column and treating with an eluting solution consisting of acetone, tetrahydrofuran and water (0–25:0–35:65–85, by volume %) to separate the extract into (−) epicatechin, (−) epigallocatechin, (−) epicatechin gallate, and (−) epigallocatechin gallate by high-performance liquid chromatography.

DETAILED DESCRIPTION OF THE INVENTION

Figure 1:
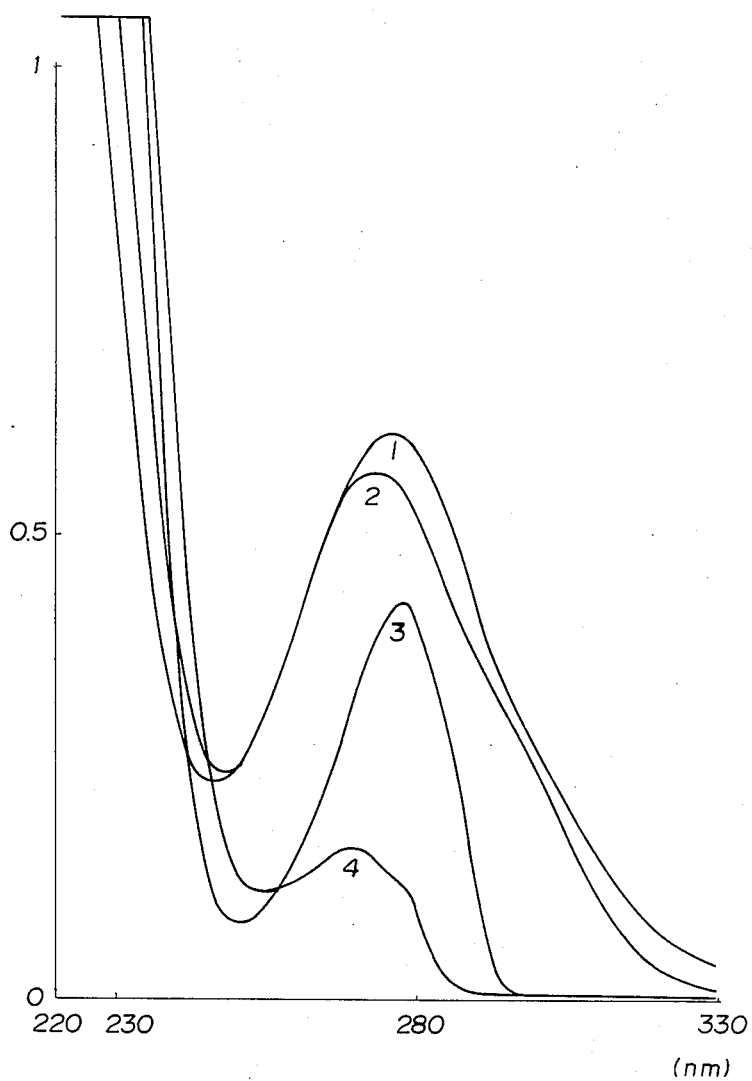
FIG. 1 is an ultraviolet absorption spectrum of the catechins produced by the present invention, in which 1 represents (−) epicatechin gallate (ECg) ($\lambda_{max}=276$ nm), 2 represents (−) epigallocatechin gallate (EGCg) ($\lambda_{max}=273$ nm), 3 represents (−) epicatechin (EC) ($\lambda_{max}32\ 278$ nm) and 4 represents (−) epigallocatechin (EGC) ($\lambda_{max}=269$ nm)
Figure 2:
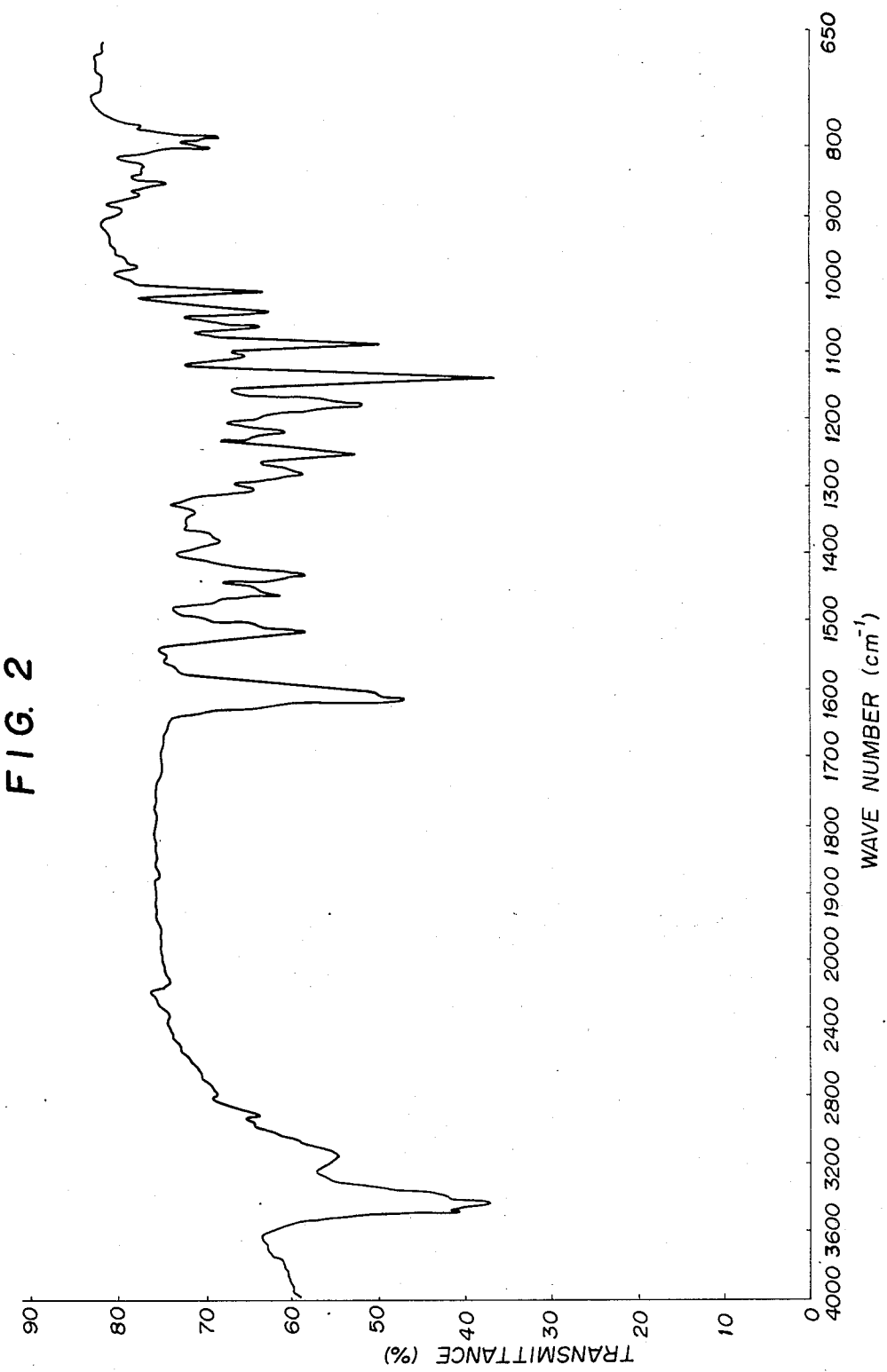
FIG. 2 is an infrared absorption spectrum of EC.
Figure 3:
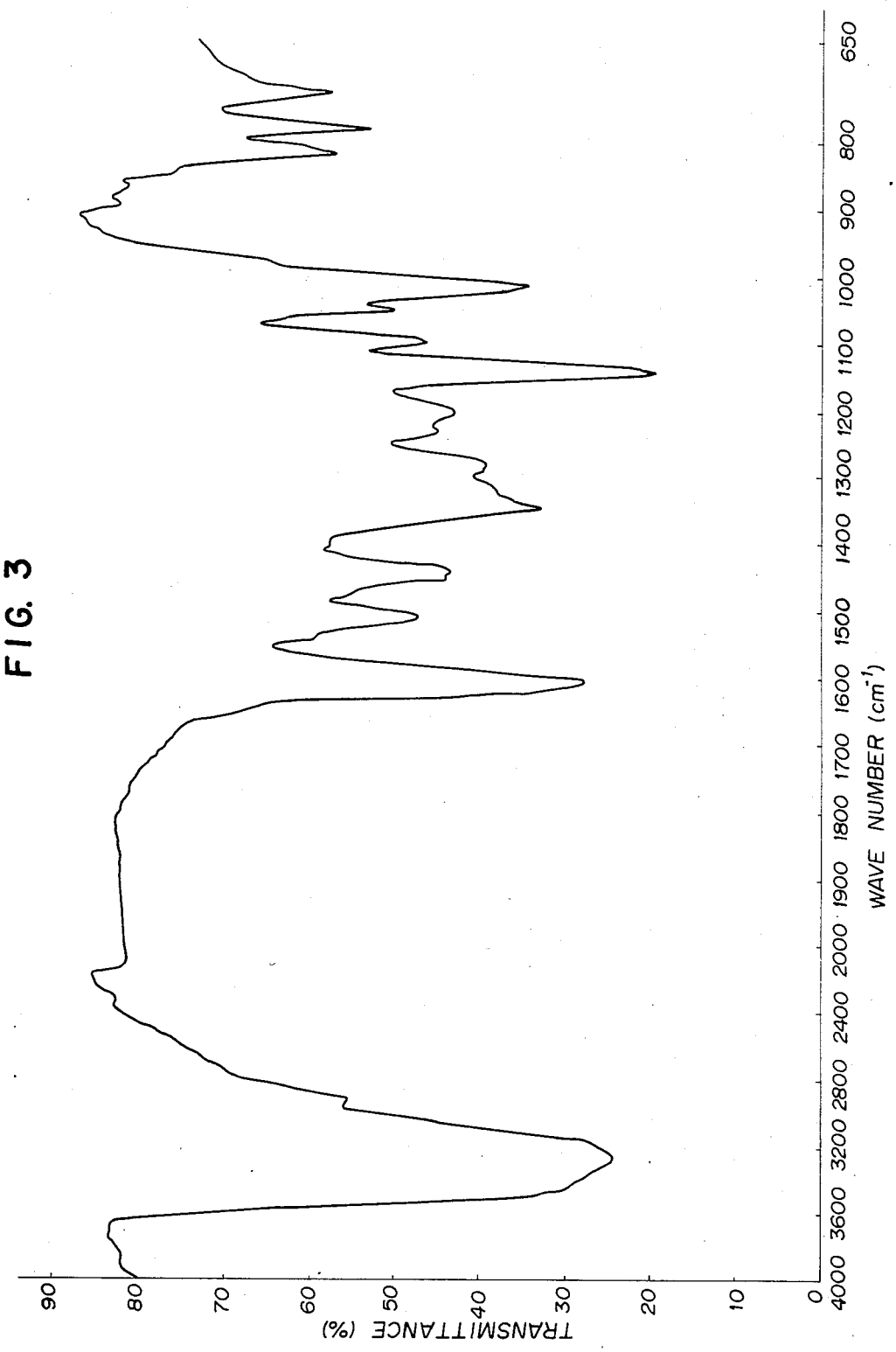
FIG. 3 is an infrared absorption spectrum of EGC.
Figure 4:
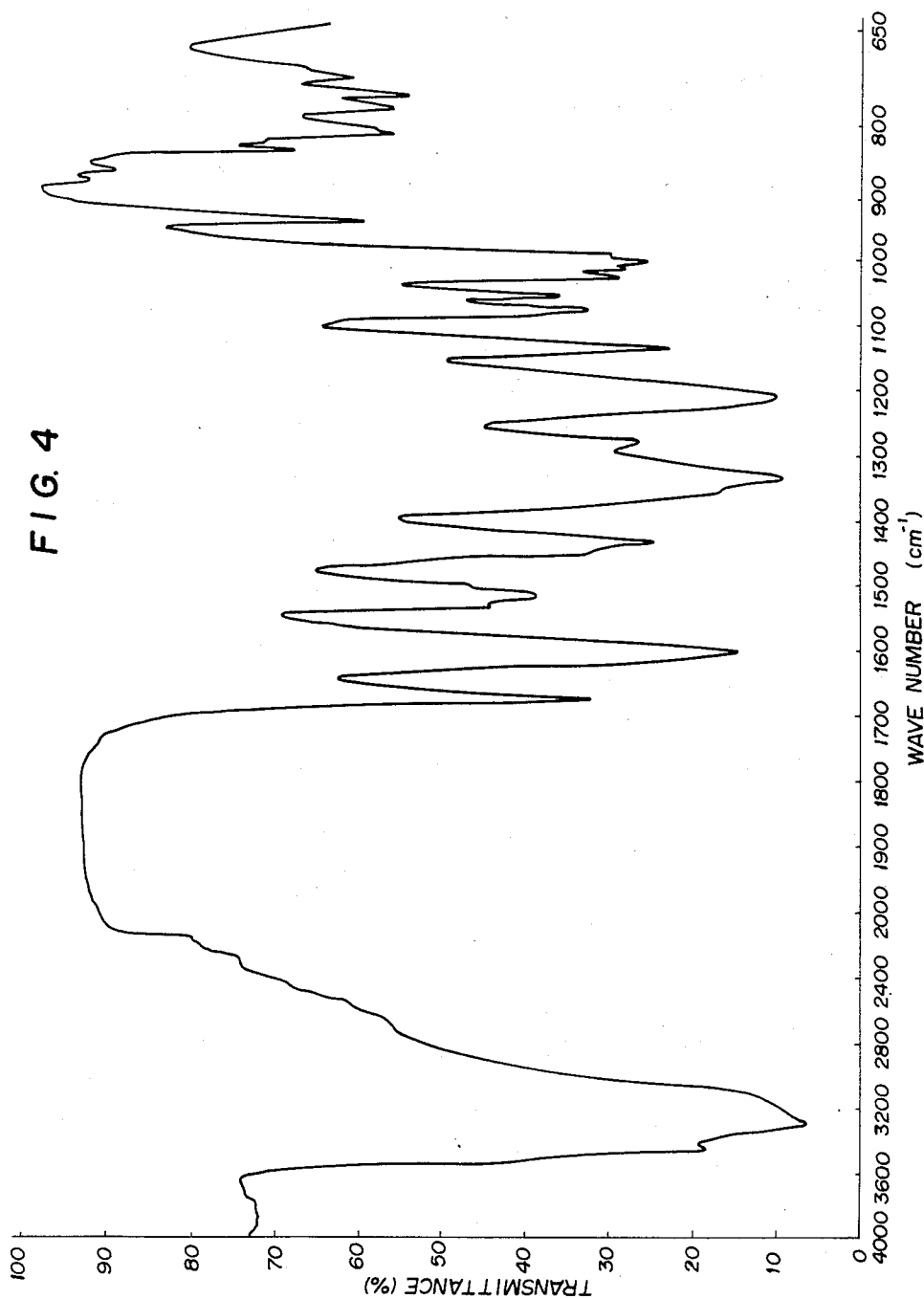
FIG. 4 is an infrared absorption spectrum of EGCg.
Figure 5:
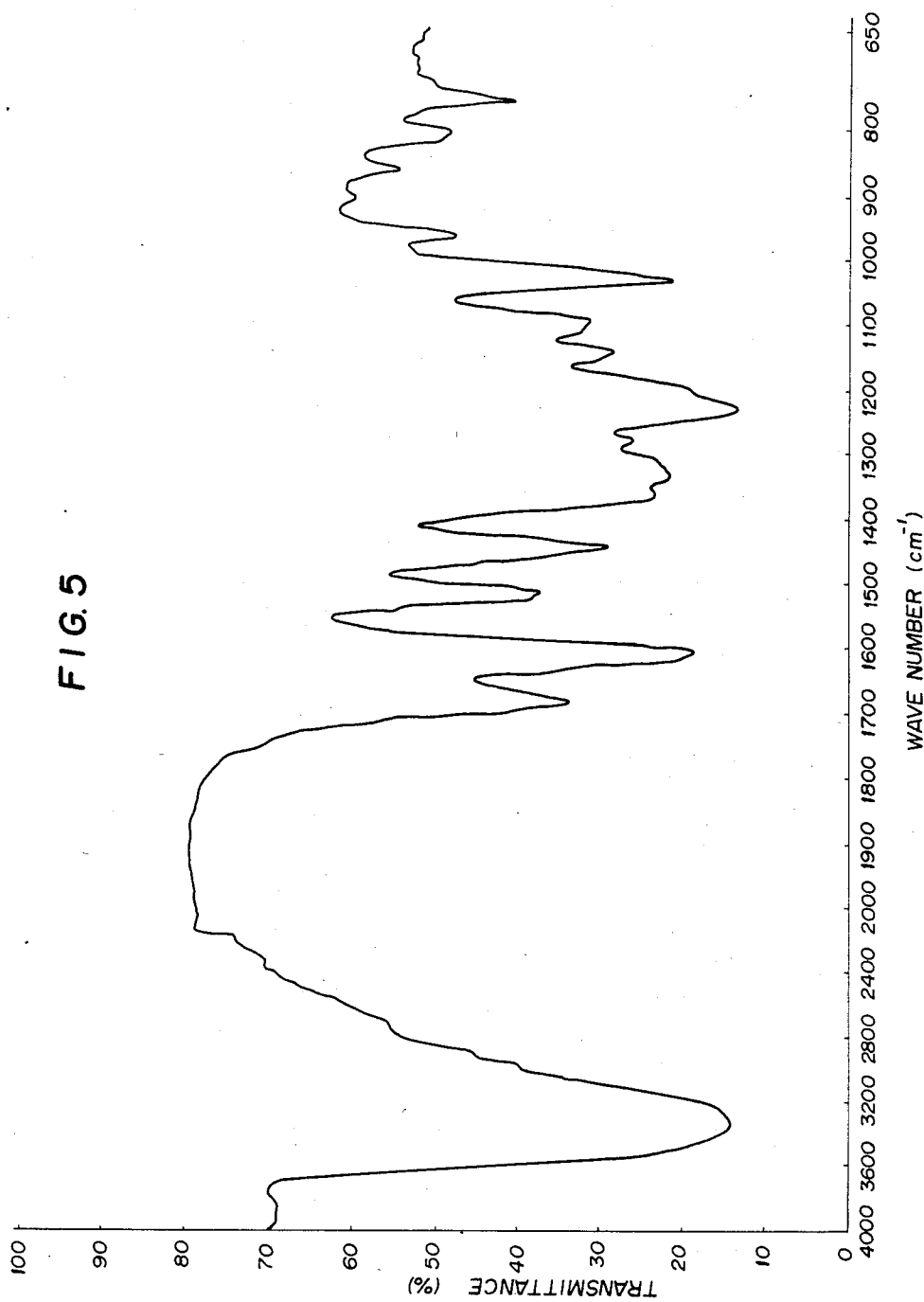
FIG. 5 is an infrared absorption spectrum of ECg.

Various types of tea leaves (except fermented tea) can be used in the present invention, i.e., unfermented tea and half-fermented tea. Examples of the unfermented tea are fresh tea leaves, green tea, instant green tea, etc., and an example of half-fermented tea is Oolong tea.

If the tea leaves are treated in the extraction process with hot water, it is preferred that the water have a temperature of at least 40° C., preferably from 80° C. to 100° C. In addition to hot water, a 40–75% aqueous solution of methanol, a 40–75% aqueous solution of ethanol, and a 30–80% aqueous solution of acetone can be used in the extraction process of the present invention. It is necessary for the concentrations of methanol, ethanol and acetone to be adjusted within the limits defined above. Outside the limits, extraction efficiency undesirably drops. If organic solvents other than methanol, ethanol and acetone are used, the same good results as in the present invention cannot be obtained. The conditions of the present extraction process are sufficient such that tea tannin containing the desired tea catechins can be extracted in sufficient amounts. Usually it is conducted for a period of at least 5 minutes, preferably from 10 minutes to 24 hours. If desired, auxiliary techniques such as agitation can be applied to shorten the extraction time.

The resulting solution containing the extract as obtained above is then washed with chloroform. The amount of chloroform to be used is preferably nearly equal to that of the solution. Washing with chloroform removes impurities such as caffeine and chlorophyll from the solution. In this case, if the impurities such as pigments are not sufficiently removed, they can be removed sufficiently by treating with a small amount of activated carbon.

The solution substantially free of the impurities as described above is then contacted with an organic solvent to transfer the extract into the organic solvent. This process can be performed in a conventional manner. Although various organic solvents can be used, it has been experimentally confirmed that ethyl acetate, n-butanol, methyl isobutyl ketone, and acetone with salting out are suitable for use in the present invention. Especially preferred are ethyl acetate and acetone with salting out.

After transferring the extract, the organic solvent is distilled away. The resulting concentrated solution is, as such or after being dried by techniques such as freeze drying and spray drying, subjected to a high-performance liquid chromatographic treatment using a reversed phase column and an eluting solution containing acetone, tetrahydrofuran and water (0–25:0–35:65–85, by volume %). This eluting solution preferably contains acetone, tetrahydrofuran and water in a % by volume ratio of 10–15:5–15:75–80.

The tea catechins are separated into four substances represented by the structural formula as described hereinabove by a high-performance liquid chromatographic treatment. The four substances which are obtained in isolated form in accordance with the present process are as follows:

(−) Epicatechin ($R_1$=H, $R_2$=H) (hereinafter abbreviated to "EC");

(−) Epigallocatechin ($R_1$=OH, $R_2$=H) (hereinafter abbreviated to "EGC");

(−) Epicatechin gallate ($R_1$=H,

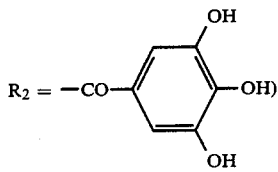

(hereinafter abbreviated to "ECg"); and (−) Epigallocatechin gallate ($R_1$=OH,

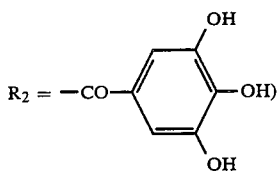

(hereinafter abbreviated to "EGCg").

An ultraviolet absorption spectrum of each substance is shown in FIG. 1, and infrared absorption spectra of the substances are shown in FIGS. 2 to 5. These analyses confirm the identity of the four substances. Each substance can be, if desired concentrated, dried and powdered, or can be purified by recrystallizing from cold water.

The tea catechins obtained by the present invention are all soluble in water and can be easily mixed with fats and oils by dissolving in a small amount of ethanol in advance.

The process of the present invention permits the economical mass-production of the tea catechins. Furthermore, the tea catechins possess a strong antioxidant action and thus can be expected to find commercial use as antioxidants for various foodstuffs, cosmetics, petroleum products, and so forth. In addition, they possess various actions such as an action to prevent fading of natural pigments, an action to control an increase of cholesterol in blood, an action to inhibit mutation, and an antibacterial action. Thus they will find a wide variety of uses.

The present invention is described in greater detail with reference to the following examples.

EXAMPLE 1

One hundred grams of instant green tea was added to 1,000 milliliters of hot water and dissolved therein thoroughly. Equal volumes of the resulting solution containing the extract and chloroform were mixed, and the solution was washed with the chloroform to remove caffeine and pigments from the solution, yielding 1,100 milliliters of an aqueous solution of the extract. This aqueous solution was treated three times with the same amount of ethyl acetate to transfer the extract into the ethyl acetate. Ethyl acetate layers were combined together and then concentrated under reduced pressure. After addition of a small amount of water, the ethyl acetate was distilled away, and there was obtained a concentrated aqueous solution. This concentrated aqueous solution was freeze dried by the usual procedure, yielding 28.9 grams of solids (a crude product). The tannin content of the solids was 72%.

Three grams of the crude product was dissolved in 20 milliliters of water, filtered by the use of a 0.45 micron filter (Millipore), and separated by high-performance liquid chromatography with a reversed phase column (Model LC 500A, cartridge column $C_{18}$, manufactured by Waters Co.) using an eluting solution containing acetone, tetrahydrofuran and water (12:10:78 by volume %), whereby each catechin was fractionated and isolated. Each fraction was concentrated under reduced pressure in a stream of nitrogen, and the thus-obtained concentrated aqueous solution was freeze dried. This treatment was repeated three times for other 3 gram-portions; that is, the treatment was performed four times each using a 3 gram-portion of the crude product. From 12 grams of the crude product were obtained 0.85 grams of EC, 1.44 grams of EGC, 1.24 grams of ECg, and 4.87 grams of EGCg; that is, 8.40 grams of the catechins were obtained. This value almost corresponds to the tannin (catechins) content of 72% as determined by the standard tannin-analyzing method.

The thus-obtained catechins were repeatedly recrystallized from small amounts of cold water and dried in vacuum, yielding white needle crystals of each catechin.

EXAMPLE 2 AND COMPARATIVE EXAMPLE

In order to determine the critical formulation of the eluting solution for separation of the peaks corresponding to the catechins, the formulation of the eluting solution for high-performance liquid chromatography in Example 1 was changed and the critical formulation was examined by the use of a liquid chromatograph analysis apparatus (differential refractometer detector RID-2AS, manufactured by Shimadzu Co., Ltd.). The results are shown in Table 1. The figures in the table represent the retention times (minutes) of the peaks, and the symbol (−) between the figures indicates that the peaks overlap.

TABLE 1

| | Acetone (%) | | | |
|---|---|---|---|---|
| | 0 | 5 | 10 | 15 |
| | Tannin | | | |
| *THF (%) | EGC EC EGCg ECg | EGC EC EGCg ECg | EGC EC EGCg ECg | EGC EC EGCg ECg |

TABLE 1-continued

| | | | | | | | | | | | | | | | | | |
|---|---|---|---|---|---|---|---|---|---|---|---|---|---|---|---|---|---|
| 0 | | | | | | | | | 10.4 | 24.0 | 36.4 | 127.0 | 6.1 | 12.0 | 16.2 | 50.0 |
| 5 | | | | | 10.2 | 21.9 | 50.8 | ∞ | 6.6 | 12.6 | 24.5 | 69.2 | 4.5 | 7.4 | 12.0 | 27.2 |
| 10 | 11.5 | 22.8 | 71.1 | ∞ | 6.8 | 12.8 | 27.6 | 71.0 | 4.7 | 7.6 | 12.8 | 28.4 | 3.7 | 5.2 | 7.1 | 13.0 |
| 15 | 7.2 | 12.7 | 32.0 | 75.0 | 5.2 | 8.1 | 15.4 | 32.0 | 4.1 | 5.9 | 8.9 | 16.0 | 3.5 | 4.6 | 5.9 | 9.3 |
| 20 | 6.1 | 9.6 | 22.7 | 43.0 | 4.3 | 6.0 | 9.6 | 16.5 | 3.6 | 4.6 | 6.2 | 9.2 | 3.0 | 3.7 | 4.5 | 6.0 |
| 25 | 4.8 | 6.8 | 12.5 | 19.7 | 3.7 | 4.8 | 6.8 | 9.9 | 3.3 | 4.0 | 4.9 | 6.5 | 2.5 | – 2.8 – 3.4 | – | 3.4 |
| 30 | 4.1 | 5.4 | 8.4 | 11.8 | 3.3 | 4.1 | 5.1 | 6.7 | 2.6 | – 2.8 – 3.1 | – | 3.5 | | | | |
| 35 | 3.6 | 4.4 | 5.9 | 7.5 | 2.7 | – 2.9 – 3.2 | – | 3.5 | | | | | | | | |
| 40 | 3.0 | – 3.4 – 4.1 | – | 4.7 | | | | | | | | | | | | |

| | Acetone (%) | | | | | | | | | | | |
|---|---|---|---|---|---|---|---|---|---|---|---|---|
| | 20 | | | | 25 | | | | 30 | | | |
| | | | | | Tannin | | | | | | | |
| *THF (%) | EGC | EC | EGCg | ECg | EGC | EC | EGCg | ECg | EGC | EC | EGCg | ECg |
| 0 | 4.2 | 7.0 | 8.6 | 21.1 | 3.2 | 4.8 | 5.5 | 10.6 | 2.9 | 3.9 | – 4.1 | 6.5 |
| 5 | 3.4 | 5.0 | 6.3 | 11.5 | 3.0 | 3.9 | 4.4 | 6.9 | | | | |
| 10 | 3.2 | 4.1 | 5.1 | 7.9 | 2.9 | 3.6 | 4.1 | 5.7 | | | | |
| 15 | 2.9 | 3.5 | 4.2 | 5.6 | 2.5 | 2.8 | – 2.8 – | 3.2 | | | | |
| 20 | 2.5 | 2.9 | – 2.9 – | 3.2 | | | | | | | | |

*THF: tetrahydrofuran

EXAMPLE 3

One hundred grams of green tea was extracted with 1,000 milliliters of a 50% aqueous ethanol solution for 10 minutes while stirring, and the tea leaves were removed by filtration, yielding about 1,000 milliliters of a filtrate. Equal volumes of the filtrate and chloroform were mixed, and the mixture was stirred to transfer caffeine and pigments into a chloroform-ethanol layer, yielding about 800 milliliters of a water-ethanol layer. This water-ethanol layer was treated three times with the same amount of ethyl acetate. These ethyl acetate layers were combined together and concentrated under reduced pressure. After addition of a small amount of water, the ethyl acetate was distilled away, yielding a concentrated aqueous solution. This concentrated aqueous solution was freeze dried, whereupon 11.9 grams of solids (a crude product) was obtained. The tannin content of the solids was 72%.

The thus-obtained crude product was treated in the same manner as in Example 1 to fractionate into each catechin. These catechins were recrystallized also in the same manner as in Example 1 and obtained in the form of crystals.

EXAMPLE 4

Two hundred grams of fresh tea leaves in which enzymes had been inactivated by steaming were mixed with 1,000 milliliters of a 70% aqueous methanol solution, agitated and ground for 10 minutes in a mixer, and was then subjected to centrifugation, yielding 770 milliliters of a supernatant. Equal volumes of the supernatant and chloroform were mixed, and the supernatant was washed with the chloroform to transfer caffeine and pigments into a chloroform-methanol layer, yielding 690 milliliters of a water-methanol layer. This water-methanol layer was treated three times with the same amount of ethyl acetate. Ethyl acetate layers were combined together and concentrated under reduced pressure. After addition of a small amount of water, the ethyl acetate was distilled away to obtain a concentrated aqueous solution. This concentrated aqueous solution was then freeze dried by the usual procedure, yielding 7.6 grams of solids (a crude product). The tannin content of the solids was 51%.

The thus-obtained crude product was treated in the same manner as in Example 1 to fractionate into each catechin. These catechins were recrystallized also in the same manner as in Example 1 and obtained in the form of crystals.

APPLICATION EXAMPLE 1

Test for Antioxidant effect on Lard

The tea catechins produced by the process of the present invention were examined for their antioxidant effect on lard (not containing any other antioxidants) according to the AOM method. The results are shown in FIG. 6 along with the test results obtained using commercially available antioxidants, dl-α-tocopherol and butylhydroxanisole (hereinafter abbreviated to "BHA").

Figure 6:
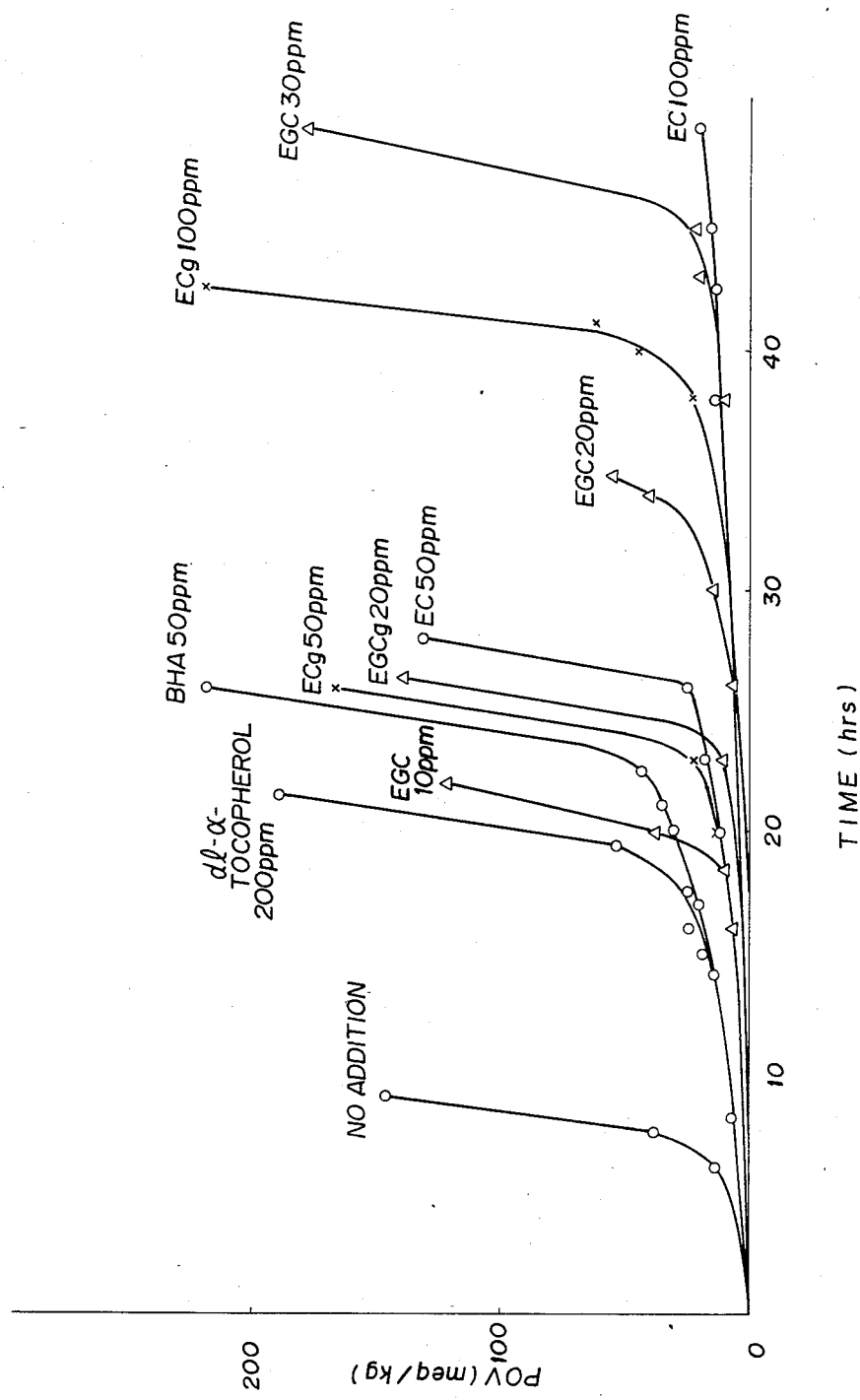
FIG. 6 is a graph showing antioxidant test results of various substances in lard.

As apparent from FIG. 6, the antioxidant effect comparable to that obtained using 200 parts per million (ppm) of dl-α-tocopherol or 50 ppm of BHA can be realized using 10 ppm of EGC, 50 ppm of ECg, 20 ppm of EGCg, or 50 ppm of EC. When the catechins are used in foodstuffs, they do not reduce the taste and color of the foodstuffs as long as the concentrations of the catechins in the ultimate food products are not more than 100 ppm.

In connection with the antioxidant effect of EGCg on lard (not containing any other antioxidants), said EGCg being a major component of the catechins, synergistic effects obtained when EGCg is used with other substances are examined and the results are shown in Tables 2 to 4.

Table 2 shows that when malic acid, citric acid and tartaric acid are each added in an amount of the 50 ppm per 10 ppm of EGCg, the antioxidant effect as determined by the usual AOM test (97.8° C.) is greatly increased.

Table 3 shows that in the modified AOM test at 60° C., the number of days required for POV to reach 20 when L-ascorbic acid, citric acid and malic acid are each added in an amount of 50 ppm per 5 ppm of EGCg is longer than that obtained when 5 ppm of EGCg alone is used.

Table 4 shows that when EGCg is used in combination with a commercially available antioxidant, Tocopherol MIX, and that the antioxidant effect is determined by the usual AOM test (97.8° C.), if 5 ppm of EGCg and 100 ppm of Tocopherol MIX are used simultaneously, there can be obtained an antioxidant effect which is much superior to that obtained when 200 ppm of Tocopherol MIX is used alone.

TABLE 2

| EGCg (ppm) | Organic Acid (ppm) | POV after 20* Hours (meq/kg) |
|---|---|---|
| 10 | — | 186 |
| 10 | Malic acid (50) | 32 |
| 10 | Citric acid (50) | 21 |
| 10 | Tartaric acid (50) | 25 |

*POV: Peroxide value

TABLE 3

| EGCg (ppm) | Organic Acid (ppm) | Days required for POV to reach 20 |
|---|---|---|
| — | — | 7.1 |
| 5 | — | 12.1 |
| — | L-Ascorbic acid (50) | 10.9 |
| 5 | L-Ascorbic acid (5) | 13.7 |
| 5 | L-Ascorbic acid (50) | 16.9 |
| 5 | Citric acid (50) | 13.8 |
| 5 | Malic acid (50) | 14.1 |

TABLE 4

| EGCg (ppm) | Tocopherol MIX (ppm) | Days required for POV to reach 20 |
|---|---|---|
| — | — | 8.0 |
| 5 | — | 14.8 |
| 5 | 100 | 29.0 |
| — | 200 | 20.0 |

APPLICATION EXAMPLE 2

Test for Determination of Anti-Fading Effect on Natural Food Colors (1) A McIlvaine's buffer (pH: 3.28) solution ($OD_{441}=0.863$) of gardenia coloring matter (water-soluble carotenoid type) was prepared. EGCg was added to the solution in an amount of: (1) 0 ppm; (2) 100 ppm; and (3) 1,000 ppm to prepare three test solutions.

Figure 7A:
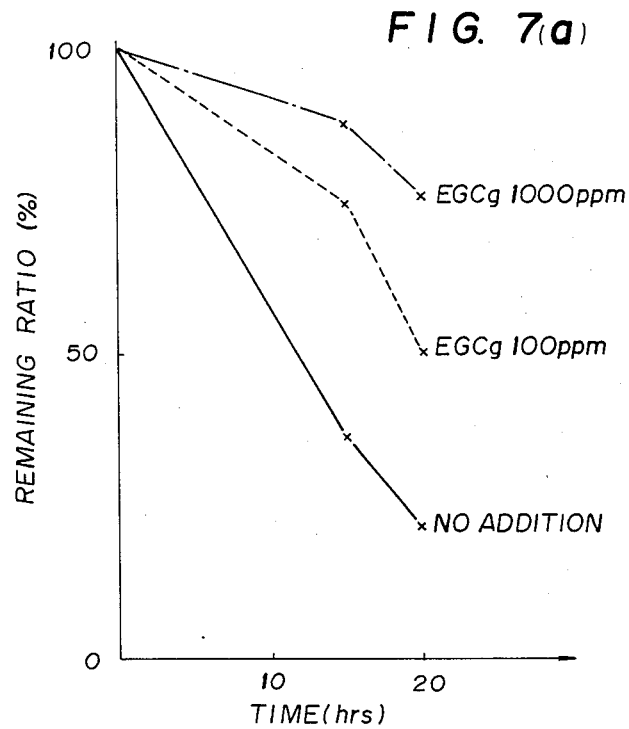
FIGS. 7(a) to 7(g) are graphs showing antifading test results of EGCg on dyes.

Each test solution was placed in a transparent test tube (diameter 1.8 centimeters; length: 18 centimeters) allowing the passage of ultraviolet rays therethrough and exposed to a 15-Watt fluorescent lamp placed at a distance of 20 centimeters, and the change of the absorbance during the lapse of time was measured. In the first place, the maximum absorption wavelenth ($\lambda_{max}$) of the test solution prior to irradiation with light was measured. Then, after irradiation with light, the absorbance at $\lambda_{max}$ was measured, and compared with the absorbance prior to irradiation. The remaining absorbance (%) was calculated based on the absorbance prior to irradiation being set at 100. The results are shown in FIG. 7(a).

(2) A methyl isobutyl ketone solution containing 6.25 ppm of β-carotene was prepared. EGCg was added to the methyl isobutyl ketone solution in an amount of: (1) 0 ppm; (2) 100 ppm; and (3) 1,000 ppm to prepare three test solutions.

Figure 7B:
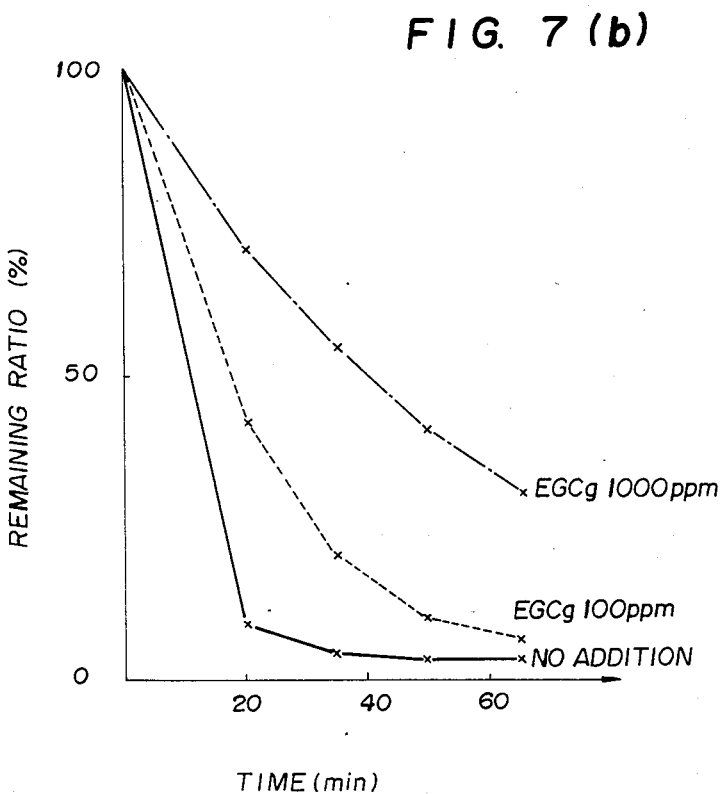
Figure 7:
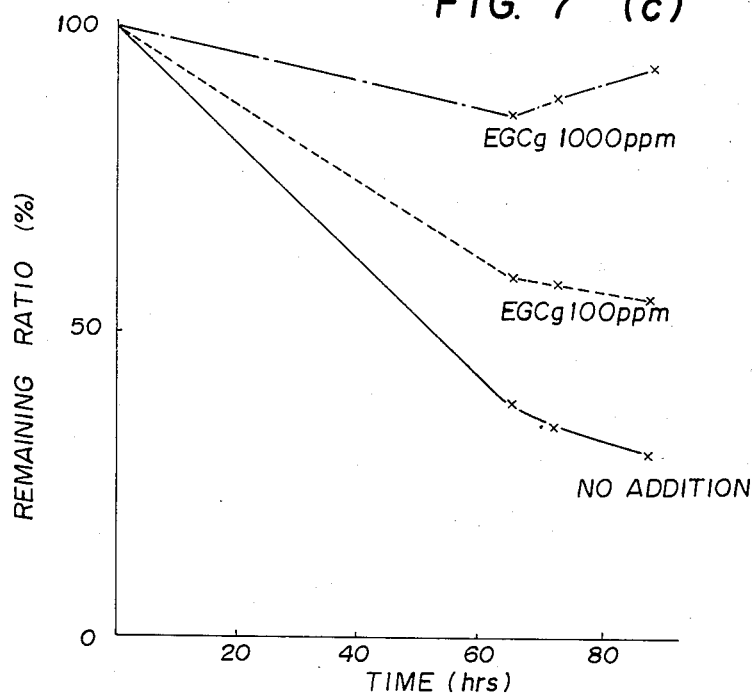
Figure 7:
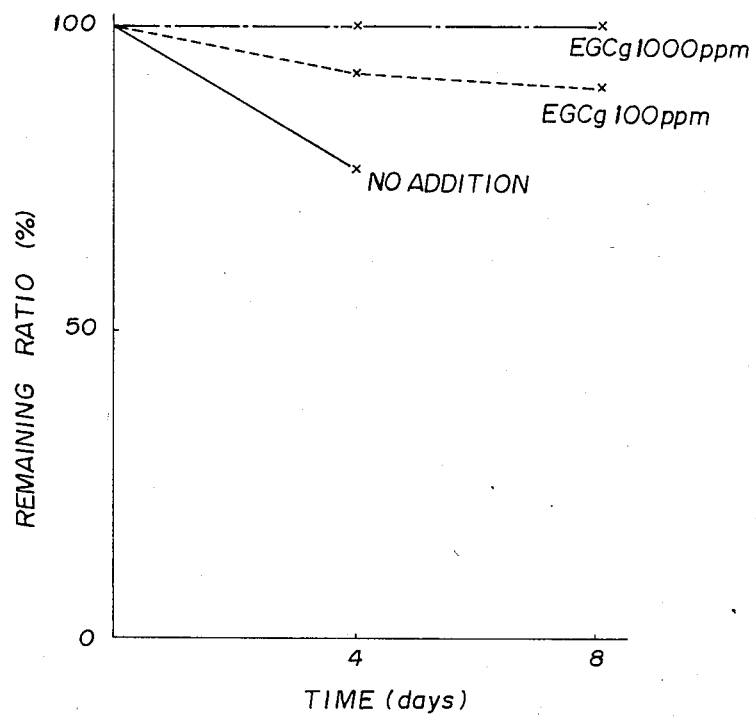

Each test solution was examined for the change during the lapse of time while exposing to a 15-Watt fluorescent lamp and a 15-Watt ultraviolet ray lamp (365 nm) as in (1) above, both being placed at a distance of 20 centimeters. The results are shown in FIG. 7(b).

(3) A McIlvaine's Buffer (pH: 3.28) solution ($OD_{390}=1.172$) of safflower coloring matter (flavonoid-chalcone type) was prepared. EGCg was added to the solution in an amount of: (1) 0 ppm; (2) 100 ppm; and (3) 1,000 ppm to prepare three test solutions.

Each test solution was examined for the change of absorbance over time while exposing the solutions to a 15-Watt fluorescent lamp and a 15-Watt ultraviolet ray lamp as in (2) above. The results are shown in FIG. 7(c).

(4) A 15% propylene glycol-containing McIlvaine's Buffer (pH: 3.28) solution ($OD_{493}=1.408$) of cochineal coloring matter (anthraquinone type) was prepared. EGCg was added to the solution in an amount of: (1) 0 ppm; (2) 100 ppm; and (3) 1,000 ppm to prepare three test solutions.

Each test solution was examined for the change in absorbance over time in the same manner as in (2) above. The results are shown in FIG. 7(d).

Figure 7E:
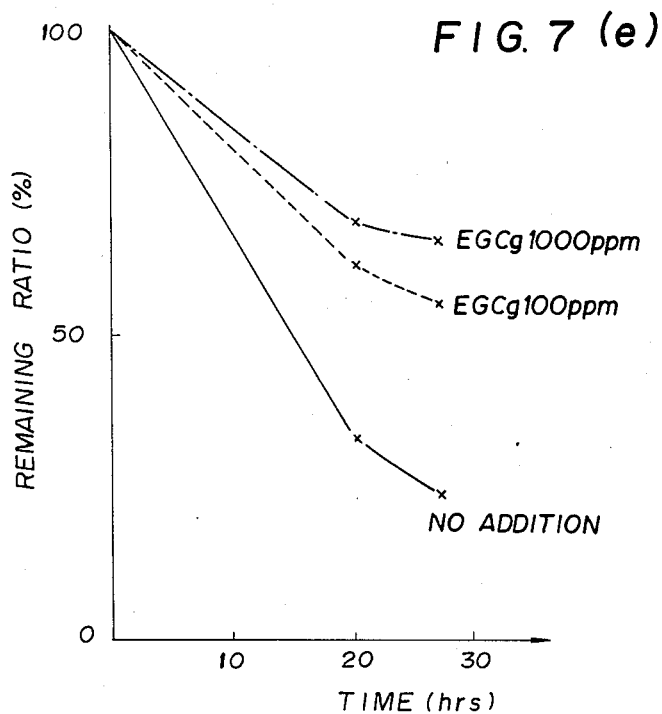

(5) A 15% propylene glycol-containing McIlvaine's Buffer (pH: 3.28) solution ($OD_{492}=0.870$) of Monascus coloring matter (azafron) was prepared. EGCg was added to the solution in an amount of: (1) 0 ppm; (2) 100 ppm; and (3) 1000 ppm. Each test solution was examined for the change in absorbance over time in the same manner as in (4) above. The results are shown in FIG. 7(e).

Figure 7F:
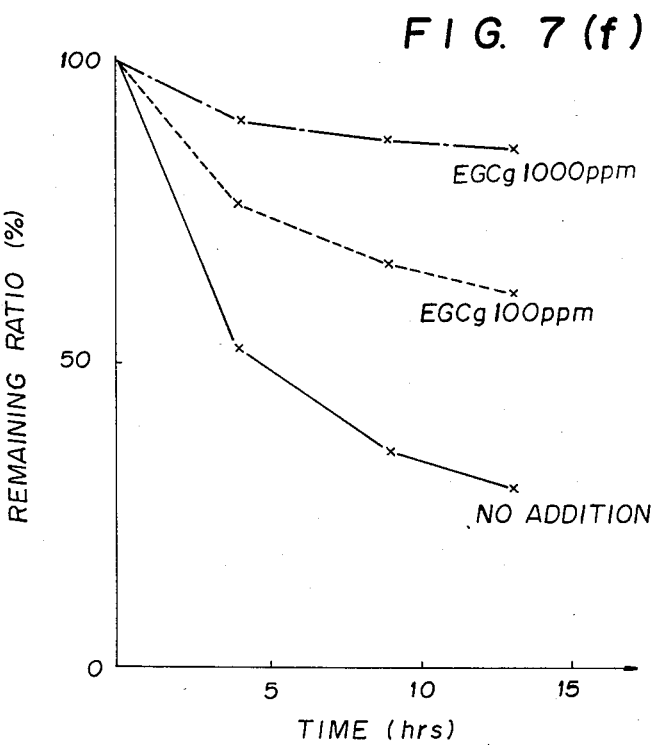
Figure 7:
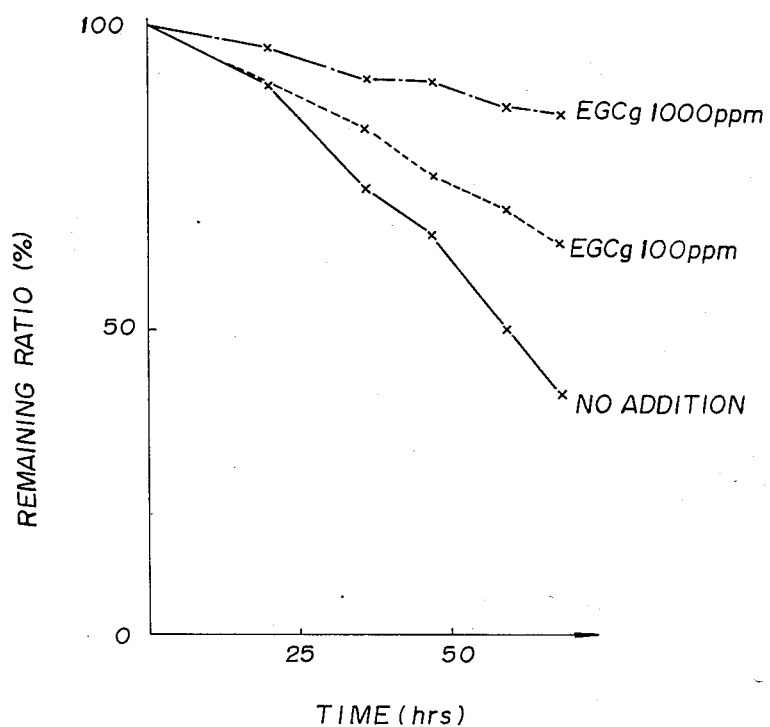

(6) A 15% propylene glycol aqueous solution ($OD_{655}=0.356$) of natural chlorophyll (as converted into the water-soluble type by adding a glycerine fatty acid ester) was prepared. Test solution were prepared in the same manner as in (4) above and were each examined for the change in absorbance over time also under the same conditions as in (4) above. The results are shown in FIG. 7(f).

(7) Using a 0.02% aqueous solution of riboflavine, three test solutions were prepared in the same manner as in (1) above. Each test solution was placed at a distance of 20 centimeters from a 100-Watt lamp and examined for the change of absorbance over time. The results are shown in FIG. 7(g).

APPLICATION EXAMPLE 3

Test of Antioxidant Effect of D-Limonene (major component of lemon oil)

The antioxidant effect of EGCg on D-limonene was examined as follows:
Gas chromatography conditions
Shimadzu Gas Chromatograph GC-9A (manufactured by Shimadzu Seisakusho Co., Ltd.)
Column (diameter: 3 millimeters; length: 2 meters) charged with 5% polyethylene glycol 6000 deposited on the carrier, chromosorb W (Acid Wash) (60–80 mesh)
A sample (0.2 microliter) was introduced into the column and the temperature was raised from 45° C. to 200° C. at a rate of 4° C. per minute.

Figure 8:
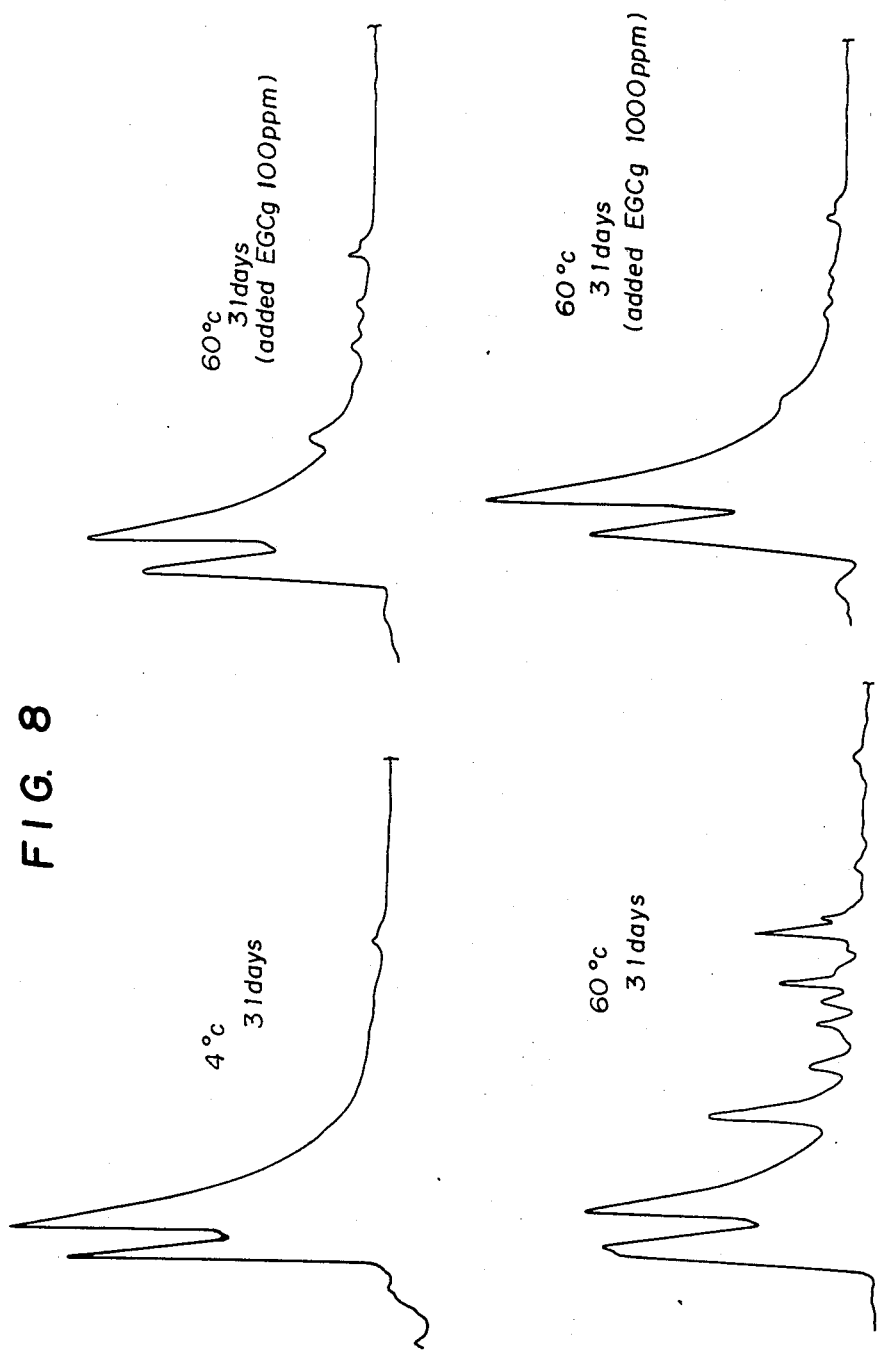
FIG. 8 is a graph showing the effect of EGCg to prevent the change with time of D-limonene.

The results are shown in FIG. 8.

This chromatographic analysis shows that when D-limonene is stored at 60° C. for 31 days, the change in peaks over time of D-limonene is due to the formation of various compounds. On the other hand, when 100 to 1,000 ppm of EGCg is added to said D-limonene, there appear peaks which are not significantly different from those when D-limonene is stored at 4° C. for 31 days. That is, it can be seen that addition of EGCg clearly controls the functional oxidative odor of D-limonene.

APPLICATION EXAMPLE 4

Figure 9:
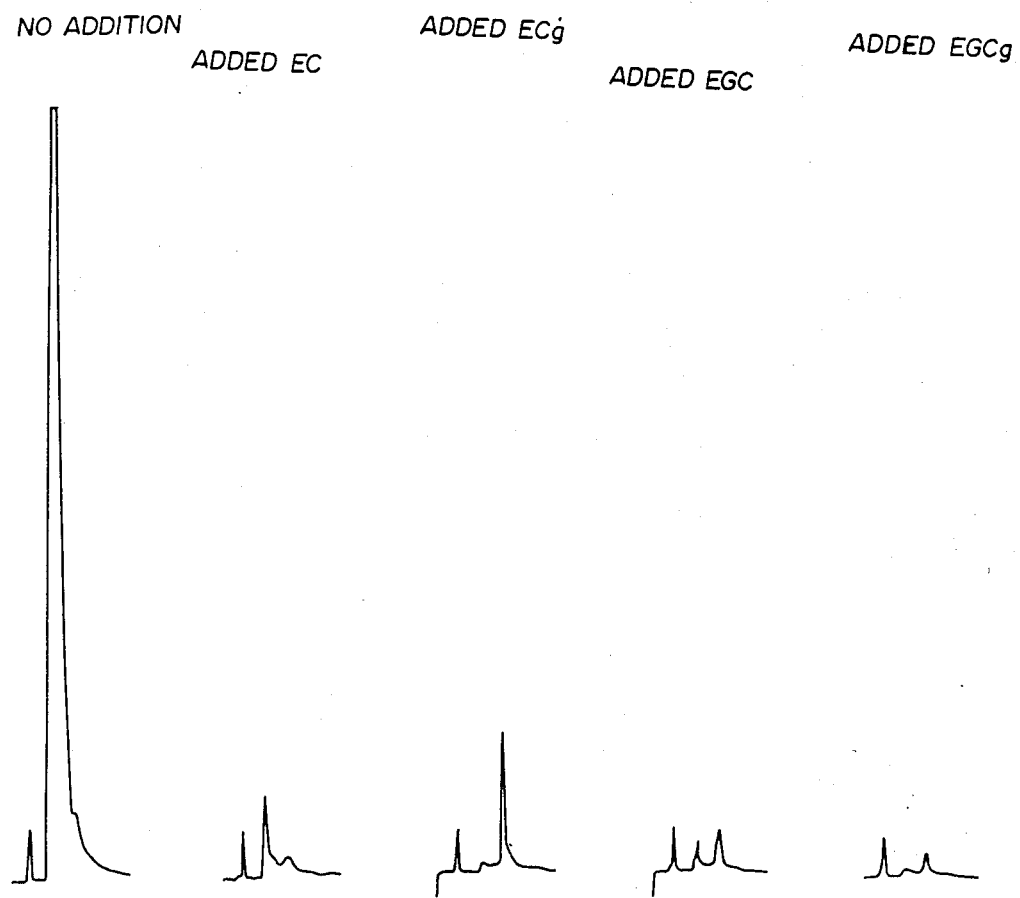
FIG. 9 is a graph showing the effect of EGCg to take the odor of trimethylamine.

The effectiveness of EGCg, EC, ECg and EGC for eliminating the putrid odor of fish due to the presence of trimethylamine (hereinafter abbreviated to "TMA") is shown in FIG. 9.

Twenty milliliters of $1\times10^{-3}$ mole TMA was placed in a 100-milliliter Erlenmeyer flask in a sealed condition, and 20 milligrams of a catechin sample was added thereto. The mixture was then stirred. After 22.5 hours, 2 milliliters of the head space was taken out of the flask, and it was then subjected to a gas chromatographic analysis using a column (diameter: 3 millimeters; length: 2 meters) charged with 15% silicone DC 550 deposited on the carrier, Diasolid L (60–80 mesh).

APPLICATION EXAMPLE 5

Twenty four Wister rats (3-weeks-old, male) were divided into four groups.
They were fed as follows:
First Group: a standard casein diet containing 25% of casein as a protein source
Second Group: a hypercholesterolemia inducing diet (prepared by adding 15% of sugar, 15% of lard, 1% of cholesterol, and 0.2% of sodium cholate to the standard casein diet)
Third Group: the diet for the second group plus 0.5% of EGCg
Fourth Group: the diet for the second group plus 1% of EGCg After four weeks, the four groups of Wister rats were subjected to 12 hour-starvation, and then blood samples were obtained from the heart of the rats. The samples were measured for the amount of cholesterol, etc. in the plasma. The results are shown in Table 5.

As can be seen from Table 5, addition of EGCg greatly inhibits the increase of the total amount of cholesterol. In particular, in the fourth group, the total amount of cholesterol was controlled to a level such that there was no significant differences (p=0.05) from the first group.

The total amount of lipids and also the total amount of cholesterol in the liver were measured, and the results are shown in Table 6. As apparent from Table 6, administration of EGCg greatly inhibited the increase in the total amounts of lipid and cholesterol.

APPLICATION EXAMPLE 6

EGCg was examined for its activity to inhibit spontaneous reverse mutations using *Bacillus subtilis* NIG 1125 (his., met. mut-1).

A shaken-culture of Bacillus subtilis NIG 1125 was carried out overnight on a Pen assay broth at 30° C. The thus-obtained microorganisms (number of living microorganisms: $1-3\times10^8$ cells/ml) (0.1 milliliter) were placed on a seminutrient culture containing a given concentration of EGCg and cultured at 30° C. for 48 hours. After the completion of culturing, the number of colonies which have undergone reverse mutation was counted and the reverse mutation frequency (F) was determined by the following equation:

$$F = \frac{\text{Number of colonies which underwent reverse mutation at a certain concentration of } EGCg}{\text{Number of living microorganisms at a certain concentration of } EGCg}$$

Figure 10:
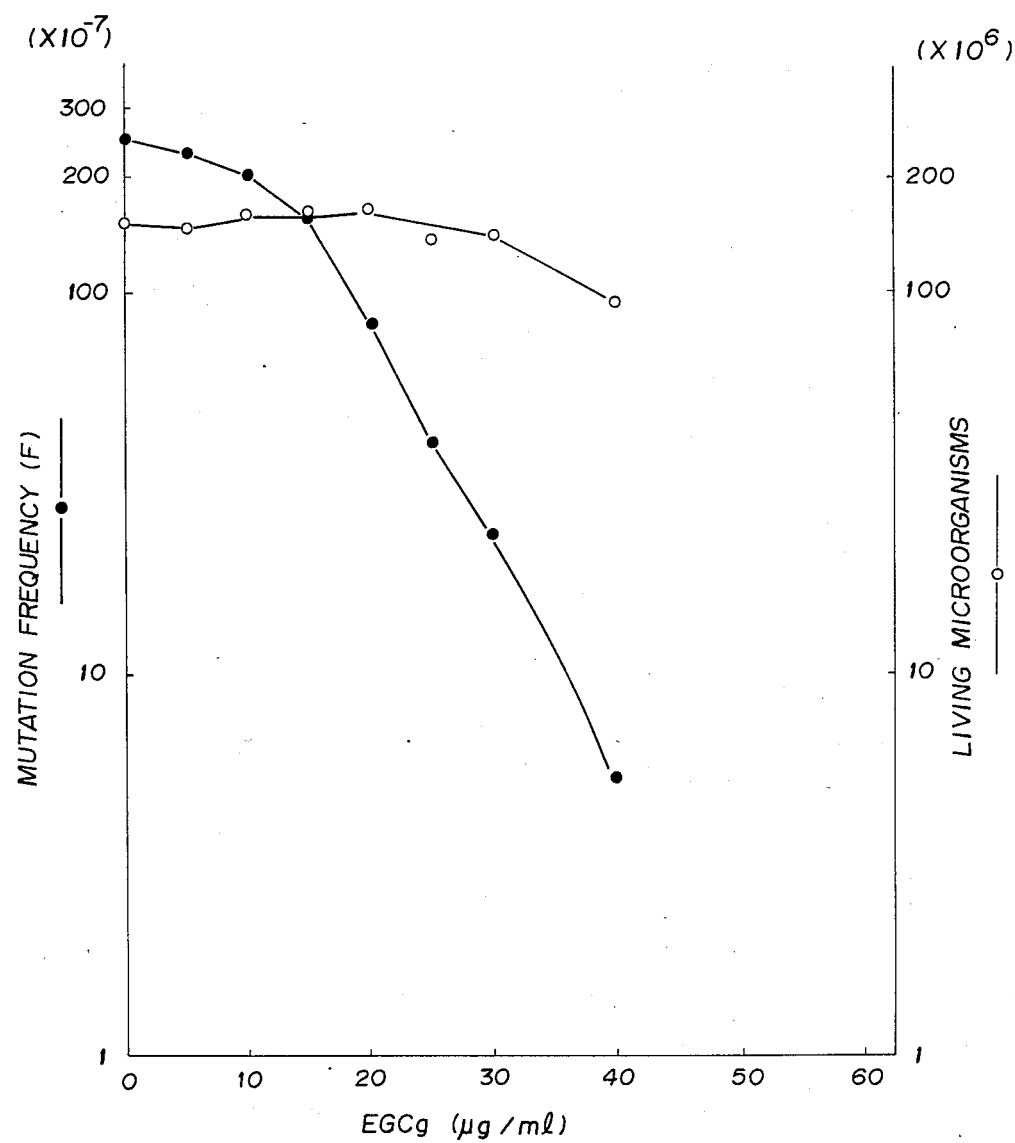
FIGS. 10 and 11 are graphs showing back mutation of nutrient requirements of microorganisms.

In FIG. 10, the reverse mutation from microorganisms requiring histidine to microorganisms which do not require histidine was examined. It can be seen that EGCg remarkably controlled the reverse mutation frequency at a concentration such that the number of living microorganisms was not affected.

Figure 11:
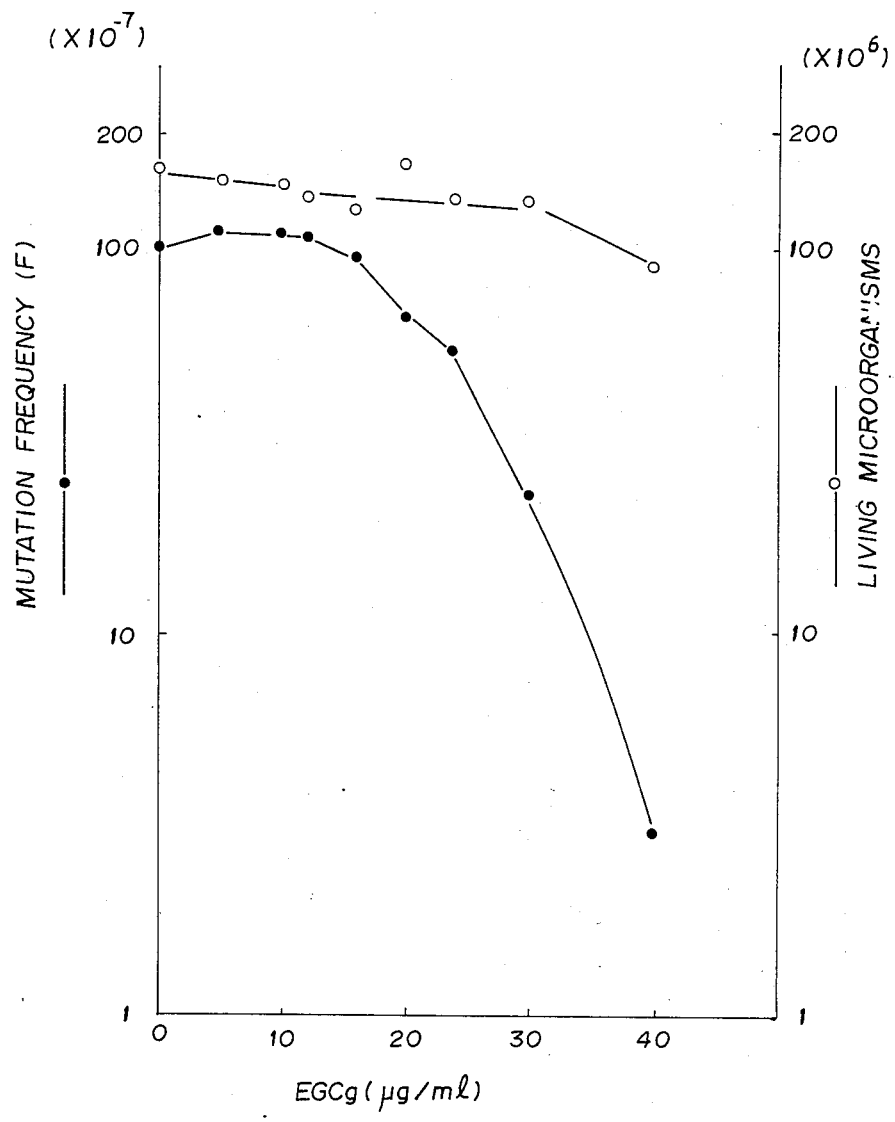

In FIG. 11, the reverse mutation from microorganisms requiring methionine to microorganisms which do not require methionine was examined. Similar results as observed for histidine were obtained.

*Bacillus subtilis NIG* 1125 (his., met. mut-1) is a DNA polymerase III temperature-sensitive strain and undergoes spontaneous reverse mutation with high frequency. It is considered, therefore, that because of the above-described EGCg's activity to inhibit reverse mutation, EGCg acts on DNA polymerase III and reduces misreplication, thereby increasing fidelity. Since DNA polymerase III is one of the important enzymes participating in chromosomal duplication, the action of EGCg on the enzyme is of interest from viewpoints of prevention of cancer, prevention of aging, and so forth.

TABLE 5

|  | First Group | Second Group | Third Group | Fourth Group |
|---|---|---|---|---|
| Hematocrit (%) | 46.5 ± 1.6 | 44.6 ± 1.0 | 43.9 ± 0.8 | 42.7 ± 0.6 |
| Hemoglobin (g/dl) | 14.65 ± 0.19 | 13.23 ± 0.10 | 13.47 ± 0.14 | 13.24 ± 0.18 |
| Total Cholesterol (mg/dl) | 93.38 ± 4.89[a] | 223.65 ± 14.26[b] | 142.78 ± 4.77[c] | 114.32 ± 8.58[a] |
| Free Cholesterol (mg/dl) | 26.69 ± 1.29 | 39.67 ± 1.72 | 28.23 ± 1.47 | 22.57 ± 1.29 |
| Total Cholesterol minus Free Cholesterol (mg/dl) | 66.68 ± 3.73 | 183.98 ± 13.26 | 114.55 ± 4.20 | 91.75 ± 7.50 |
| HDL-Cholesterol (mg/dl) | 53.46 ± 2.94 | 21.56 ± 1.45 | 31.06 ± 1.45 | 29.70 ± 1.07 |
| LDL-Cholesterol (mg/dl) | 11.30 ± 0.81 | 163.77 ± 10.52 | 85.27 ± 4.60 | 53.94 ± 4.83 |
| Triglyceride (mg/dl) | 162.72 ± 7.13[a] | 92.08 ± 8.01[b] | 74.12 ± 6.05[b] | 71.89 ± 8.87[b] |

[a], [b], [c]: indicate level of significance at p = 0.05.

TABLE 6

| Group | Total Lipid (%) | Total Cholesterol (mg/m · liver) | Liver Wet Weight (g) |
|---|---|---|---|
| First Group | 5.20 ± 0.13 | 4.83 ± 0.11 | 7.50 ± 0.28[a] |
| Second Group | 32.95 ± 0.69[a] | 106 ± 3[a] | 11.91 ± 0.47[b] |
| Third Group | 28.73 ± 0.81[b] | 84 ± 2[b] | 12.76 ± 0.46[b] |
| Fourth Group | 23.99 ± 0.57[c] | 71 ± 3[c] | 10.61 ± 0.17[b] |

[a], [b], [c]: indicate level of significance at p = 0.05

APPLICATION EXAMPLE 7

EGC and EGCg were measured for the minimum inhibitory concentration (MIC) against various microorganisms.

As apparent from Table 7, EGC and EGCg exhibit a bactericidal action when added in an amount of from 200 to 500 ppm based on the weight of the culture medium. Thus they are expected to find commercial use as antiseptics for foodstuffs. On the other hand, they do not exhibit a definite bactericidal action against yeasts.

The minimum inhibitory concentration was measured as follows:

A culture medium (pH, 7.2) consisting of 8 grams of a commercially available nutrient broth, 15 grams of agar, and 1,000 milliliters of water was used as a basic culture medium for bacteria. A culture medium (pH, 5.0-6.0) consisting of 40 grams of potato dextrose agar and 1,000 milliliters of distilled water was used as a basic culture medium for yeast. EGC or EGCg was added to Petri dishes, each containing 20 milliliters of the basic bacteria culture medium, in 13 stepwise varied concentrations between 1 to 500 ppm (provided each two dishes contained the same concentration of EGC or EGCg) for bacteria. On the other hand, for yeasts, EGC or EGCg was added to Petri dishes, each containing 20 milliliters of the basic yeast culture medium, in 12 stepwise varied concentrations between 5 and 800 ppm (provided each two dishes contained the same concentration of EGC or EGCg). In the case of bacteria, each dish was inoculated with 8 strains in a radial form, and in the case of yeasts, each dish was inoculated with 5 strains in a radial form. They were incubated in the usual manner to determine the minimum inhibitory concentration.

TABLE 7

|  | EGC (ppm) | EGCg (ppm) |
| --- | --- | --- |
| Staphylococcus aureus IAM1011 | 300 | 200 |
| Escherichia coli IAM12119 | 300 | 500 |
| Bacillus subtilis IAM12118 | >500 | >500 |
| Pseudomonas aerginosa IAM1054 | 200 | 500 |
| Pseudomonas fluorescens IAM12022 | 200 | 500 |
| Serratia marcescens IAM1104 | 500 | >500 |
| Proteus vulgaris IAM1025 | 200 | 200 |
| Enterobacter aerogenes IAM1183 | 200 | 300 |
| Saccharomyces cerevisiae IAM4274 | >800 | >800 |
| Saccharomyces rouxii IAM4962 | " | " |
| Pichia membranaefaciens IAM4911 | " | " |
| Hansenula anomala IAM4967 | " | " |
| Schizosaccharomyces pombe IAM4779 | " | " |

What is claimed is:

1. A process for producing tea catechins selected from the group consisting of (−) epicatechin, (−) epigallocatechin, (−) epicatechin gallate, and (−) epigallocatechin gallate, which comprises the steps of
   extracting tea leaves selected from the group consisting of unfermented tea and half-fermented tea with hot water or a solvent selected from a group consisting of a 40-75% aqueous solution of methanol, a 40-75% aqueous solution of ethanol and a 30-80% aqueous solution of acetone to obtain an extract-containing solution;
   washing the extract-containing solution with chloroform;
   contacting the washed solution with an organic solvent selected from the group consisting of ethyl acetate, n-butanol, methyl isobutyl ketone, and acetone to transfer the extract into said organic solvent;
   distilling away the organic solvent to yield a concentrated solution containing the extract; and
   passing the extract through a reversed phase column in the presence of an eluting solution consisting essentially of 0-25 volume % of acetone, 0-35 volume % of tetrahydrofuran and 65-85 volume % of water to thereby obtain said tea catechins.

2. The process as claimed in claim 1, wherein the unfermented tea is selected from the group consisting of fresh tea leaves, green tea and instant green tea.

3. The process as claimed in claim 1, wherein said organic solvent is ethyl acetate or acetone.

4. The process as claimed in claim 1, wherein said eluting solution consists essentially of 10-15 volume % of acetone, 5-15 volume % of tetrahydrofuran and 75-80 volume % of water.

5. The process as claimed in claim 1, wherein the tea leaves are extracted with hot water at a temperature of 80°-100° C.

6. The process as claimed in claim 1, wherein the step of extracting said tea leaves is conducted for at least five minutes.

7. The process as claimed in claim 1, wherein the chloroform is used in an amount approximately equal to the amount of the extract containing solution.

8. The process as claimed in claim 1 further comprising freeze drying or spray drying the concentrated solution containing the extract and eluting said extract.

9. The process as claimed in claim 1, wherein said concentrated solution containing the extract is passed through said reversed phase column in the presence of said eluting solution.

10. The process as claimed in claim 1, wherein said eluting solution consists essentially of 10-15 volume % of acetone, 5-15 volume % of tetrahydrofuran and 75-80 volume % of water.

11. The process as claimed in claim 10, wherein the chloroform is used in an amount approximately equal to the amount of the extract containing solution.

12. The process as claimed in claim 11, further comprising freeze drying or spray drying the concentrated solution containing the extract and eluting said extract.

13. The process as claimed in claim 12, wherein said eluting solution consists essentially of 10-15 volume % of acetone, 5-15 volume % of tetrahydrofuran and 75-80 volume % of water.

14. The process as claimed in claim 13, wherein the tea is unfermented tea selected from the group consisting of fresh tea leaves, green tea and instant green tea.

15. The process as claimed in claim 5, wherein said eluting solution consists essentially of 10-15 volume % of acetone, 5-15 volume % of tetrahydrofuran and 75-80 volume % of water.

16. The process as claimed in claim 15, wherein the chloroform is used in an amount approximately equal to the amount of the extract containing solution.

17. The process as claimed in claim 16, further comprising freeze drying or spray drying the concentrated solution containing the extract and eluting said extract.

18. The process as claimed in claim 17, wherein the tea is unfermented tea selected from the group consisting of fresh tea leaves, green tea and instant green tea.

* * * * *